(12) United States Patent
Lacson et al.

(10) Patent No.: US 10,789,939 B2
(45) Date of Patent: Sep. 29, 2020

(54) WEARABLE WORD COUNTER

(71) Applicant: The University of Chicago, Chicago, IL (US)

(72) Inventors: Alvin Lacson, Portola Valley, CA (US); Jill Desmond, Portola Valley, CA (US); Andy Turk, Portola Valley, CA (US); Jon Boggiano, Portola Valley, CA (US); Jonathan Simon, Portola Valley, CA (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/168,452

(22) Filed: Oct. 23, 2018

(65) Prior Publication Data

US 2019/0122652 A1 Apr. 25, 2019

Related U.S. Application Data

(63) Continuation-in-part of application No. 15/191,688, filed on Jun. 24, 2016, now Pat. No. 10,134,424.

(Continued)

(51) Int. Cl.
*G10L 15/04* (2013.01)
*G10L 15/05* (2013.01)
*G10L 15/02* (2006.01)
*G10L 15/22* (2006.01)
*G01S 3/00* (2006.01)
(Continued)

(52) U.S. Cl.
CPC ............ *G10L 15/05* (2013.01); *A61B 5/1118* (2013.01); *G01S 3/00* (2013.01); *G10L 15/02* (2013.01); *G10L 15/22* (2013.01); *A61B 5/4809* (2013.01); *A61B 2560/0209* (2013.01); *A61B 2560/0242* (2013.01); *G10L 17/00* (2013.01); *G10L 25/51* (2013.01); *G10L 2015/027* (2013.01)

(58) Field of Classification Search
None
See application file for complete search history.

(56) References Cited

U.S. PATENT DOCUMENTS 6,185,527 B1 2/2001 Petkovic
6,208,970 B1 3/2001 Ramanan
(Continued)

FOREIGN PATENT DOCUMENTS

DE 10212128 A1 10/2003

OTHER PUBLICATIONS

Betty Hart & Todd R. Risley, Meaningful Differences in the Everyday Experience of Young American Children (pp. vii, 21-49, 58-59, 64-67, 72-75, 132-133, 234-235, 238-241), 1995, Paul H. Brookes Publishing Co., Baltimore, MD.

*Primary Examiner* — Satwant K Singh
(74) *Attorney, Agent, or Firm* — Travis R. Banta; TechLaw Ventures, PLLC

(57) ABSTRACT

This disclosure generally relates to a word counting device. Specifically, this disclosure generally relates to a wearable word counter device. The word counter device includes a microphone to receive speech input. The word counter device further includes a light sensor to receive data representative of an amount of light in an environment of the word counter device. The word counter device also includes an accelerometer to receive data representative of an amount of movement of the word counter device or the wearer of the word counter device.

14 Claims, 2 Drawing Sheets

Related U.S. Application Data

(60) Provisional application No. 62/184,291, filed on Jun. 25, 2015.

(51) Int. Cl.
*A61B 5/11* (2006.01)
*G10L 25/51* (2013.01)
*A61B 5/00* (2006.01)
*G10L 17/00* (2013.01)

(56) References Cited

U.S. PATENT DOCUMENTS

| | | |
|---|---|---|
| 6,990,445 B2 | 1/2006 | Ky |
| 8,976,941 B2 | 3/2015 | Kim |
| 9,190,060 B2 | 11/2015 | Nonaka |
| 9,390,709 B2 | 7/2016 | Nonaka |
| 9,530,401 B2 | 12/2016 | Kim |
| 9,548,046 B1 | 1/2017 | Boggiano |
| 9,763,571 B2 * | 9/2017 | Kozloski ............... A61B 3/0025 |
| 9,962,118 B2 * | 5/2018 | Kozloski ............... A61B 5/4064 |
| 9,968,287 B2 * | 5/2018 | Kozloski ............... A61B 5/4064 |
| 2002/0169583 A1 | 11/2002 | Gutta |
| 2003/0220788 A1 | 11/2003 | Ky |
| 2007/0185704 A1 | 8/2007 | Yoshimura |
| 2009/0043581 A1 | 2/2009 | Abbott |
| 2010/0217591 A1 | 8/2010 | Shpigel |
| 2013/0322215 A1 | 12/2013 | Du |
| 2014/0123311 A1 * | 5/2014 | Pegg ........................ G06F 21/10 726/27 |
| 2014/0244255 A1 | 8/2014 | Nonaka |
| 2016/0278633 A1 * | 9/2016 | Kozloski ................ A61B 3/112 |
| 2016/0278666 A1 * | 9/2016 | Kozloski ............... A61B 5/4064 |
| 2016/0278686 A1 * | 9/2016 | Kozloski ................ A61B 5/16 |
| 2016/0371240 A1 * | 12/2016 | McKaughan ......... G06F 40/205 |

* cited by examiner

# WEARABLE WORD COUNTER

This application is a Continuation-In-Part of and claims priority to U.S. patent application Ser. No. 15/191,688, filed Jun. 24, 2016, which claims priority to U.S. Provisional Patent Application No. 62/184,291, filed on Jun. 25, 2015, which are incorporated by reference in their respective entireties.

BACKGROUND

1. Technical Field

This disclosure relates generally to a wearable device. More specifically, the device disclosed herein relates to a device that may be worn by a user to count a number of words heard by or spoken to the user over a period of time.

2. Description of the Related Art

Child rearing and development is often one of the most daunting tasks that new parents face. However, many parents simply lack the knowledge and tools to objectively track a child's development in the child's early years when brain development is most rapid. Moreover, recent studies have shown a correlation between brain development in young children and the degree of interaction they have with parents and others. Specifically, a high degree of correlation exists between the quantity of words spoken to a baby and brain development in children younger than three years old. Given that the number of words spoken to a baby predicts a baby's intelligence and that a person's intelligence stabilizes for life by pre-school, the number of words spoken to a child between birth and age three largely sets the child's mental ability trajectory for the child's lifetime.

In order to track the number of words spoken to children for these studies, researchers used cassette tapes or digital speech recorders to record conversations in the homes of young children. Once the recordings were completed, researchers tediously transcribed the recordings and manually counted each word heard by or spoken to a young child. This method of counting words spoken to a child is profoundly inefficient in terms of effort and time effectiveness. While these technologies made it possible to manually count the words spoken to a child they are inadequate to do any more than make a recording of conversations for later transcription. Other more rudimentary methods for counting the number of words heard by or spoken to a child have also included an observer manually counting words as the words are spoken to a child.

One difficulty in monitoring the number of words spoken to a child is that between birth and three years of age, most children become ambulatory and move away from, and out of recording range of, conventional stationary recording devices. However, with the advent of wearable devices, also known as "wearables," mobile processing power has been substantially increased allowing previously stationary devices to become portable. As processing power per unit of physical space has increased, wearables have gained in popularity with the general public by incorporating processing power into articles of clothing or devices that attach to the head, hands, feet, arms, legs, or other body parts of their users. Several examples of wearable devices include a calculator wristwatch, eye glasses that incorporate heads-up displays, ear muffs or hats that incorporate head phones or ear buds, smart watches, smart headbands, smart pedometers, and a host of other implementations that provide various users with desired information or entertainment. Many wearable devices have been implemented as health care or health monitoring devices and are used to monitor heart rate, blood pressure, physical activity levels, body temperature, and other physical indications for the ill and for high performance athletes.

It is therefore one object of this disclosure to provide a wearable device that counts the number of words spoken to or heard by a user in real-time. Another object of this disclosure is to provide a wearable word counting device to count the number of words spoken to or heard by a user and transmit a real-time word count to another device. Another object of this disclosure is to provide a wearable device that streams information to a remote device with greater processing power. Another object of this disclosure is to provide a wearable device capable of performing speech analysis in a low-power environment.

SUMMARY

Consistent with embodiments disclosed herein, a word counter device is disclosed. The word counter device includes a microphone to receive speech input. The word counter device further includes a light sensor to receive data representative of an amount of light in an environment of the word counter device. The word counter device also includes an accelerometer to receive data representative of an amount of movement of the word counter device or the wearer of the word counter device.

Also disclosed herein is a word counter system. The word counter system includes a word counter device which comprises a microphone to receive speech input. The word counter device further includes a light sensor to receive data representative of an amount of light in an environment of the word counter device. The word counter device also includes an accelerometer to receive data representative of an amount of movement of the word counter device or the wearer of the word counter device. The word counter system includes a mobile device which may receive the speech input, the data representative of an amount of light in an environment of the word counter device, and data representative of an amount of movement of the word counter device or the wearer of the word counter device.

BRIEF DESCRIPTION OF THE DRAWINGS

The accompanying drawings illustrate an embodiment of a wearable word counter.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
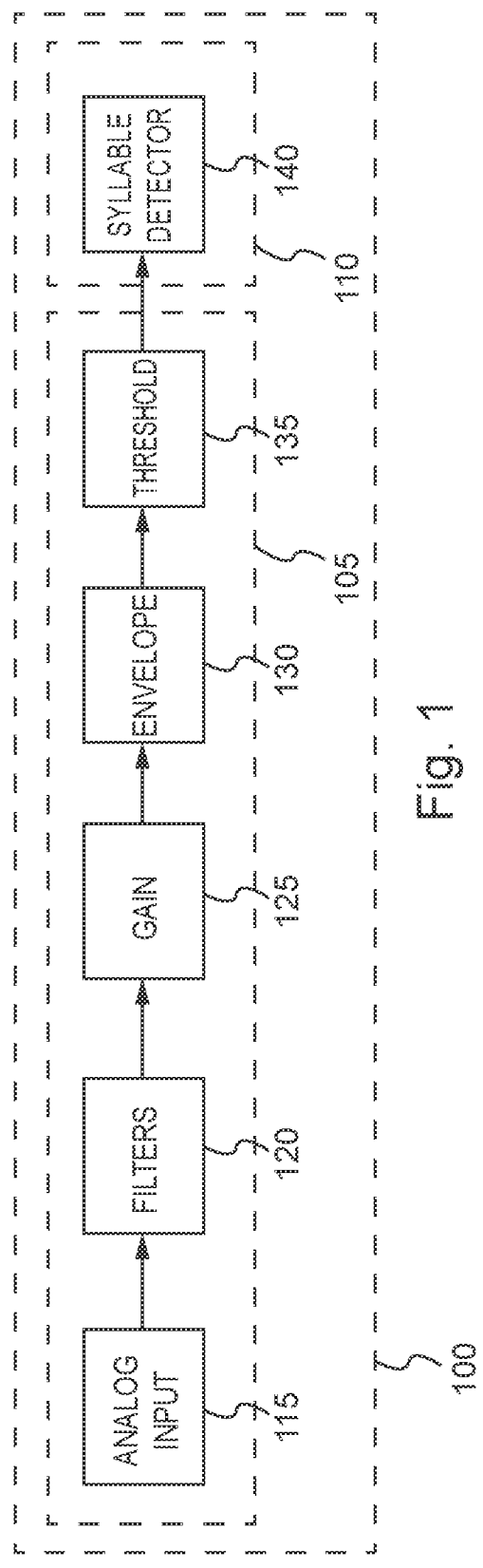
FIG. 1 illustrates a block circuit diagram of the wearable word counter.

FIG. 1 illustrates a block circuit diagram of wearable word counter 100. Wearable word counter 100 includes an analog low power circuit 105 that is coupled to a digital microcontroller circuit 110. In one embodiment, wearable word counter 100 includes a battery, not shown, which supplies power to both analog low power circuit 105 and digital microcontroller circuit 110. During use, the battery within wearable word counter 100 supplies power sufficient for analog low power circuit 105 and digital microcontroller circuit 110 to operate for an extended time period. For example, in one mode of operation, the battery within wearable word counter 100 supplies sufficient power for wearable word counter 100 to operate for a period of up to a week. The battery within wearable word counter 100 may be a rechargeable battery, allowing the battery within wearable word counter 100 to be recharged during periods of non-use.

In use, wearable word counter 100 is portable. For example, wearable word counter 100 may be attached to a user, such as a child, or, alternatively, attached to the user's clothing. Thus, in one embodiment, wearable word counter 100 may be attached to the user or the user's clothing in a way that does not restrict the ability of the user to move or play. Wearable word counter 100 may further be positioned on the user or user's clothing such that it may be unobstructed to the aural environment of the user to whom it is attached. Wearable word counter 100 may move with the user as the user travels in a physical environment. In one embodiment, wearable word counter 100 may be removed when the user sleeps because a user is generally not perceptive of sounds during sleep.

Because wearable word counter 100 is portable and powered by a battery, it is advantageous that battery power consumed by wearable word counter 100 is minimized. Accordingly, wearable word counter 100 reduces power consumption by implementing analog low power circuit 105. Analog low power circuit 105 consumes far less battery power than other technologies, such as a digital signal processor, and others, while providing sufficient functionality to detect individual words spoken to a user of wearable word counter 100. Thus, at least one advantage of wearable word counter 100 is that analog low power circuit 105 consumes very little battery power. In general, a physical size of a battery is proportional to the amount of electrical voltage and electrical current produced by the battery. Accordingly, because wearable word counter 100 utilizes analog low power circuit 105, the physical size of wearable word counter 100 may be substantially smaller than a similar device that utilizes digital signal processing technology. A smaller physical size for wearable word counter 100 is less cumbersome to a user, interferes less with the user's movement, and is lighter allowing the user to bear the weight of wearable word counter 100 more easily. Wearable word counter 100 may be implemented with each of the elements shown in FIG. 1 in a single housing.

Figure 2:
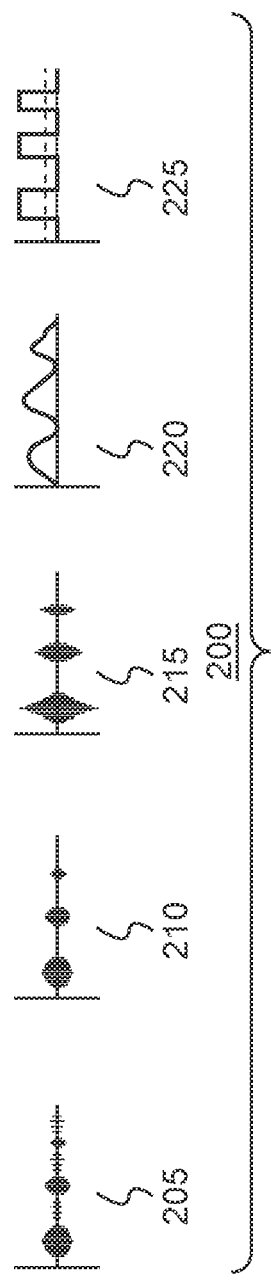
FIG. 2 illustrates a series of waveforms representative of various stages of the block circuit diagram illustrated in FIG. 1.

Analog low power circuit 105 within wearable word counter 100 includes an analog input receiver 115, linear analog filters 120, a gain amplifier stage 125, an envelope detector 130, and a threshold detector 135. FIG. 2 shows a series of waveforms 200 that are used herein to explain the elements of analog low power circuit 105.

For example, analog input receiver 115 may be implemented as a microphone installed within wearable word counter 100 that receives analog input, such as a speech signal. In this embodiment, the microphone within analog input receiver 115 may be positioned within wearable word counter 100 in such a way as to be relatively unobstructed from the user's aural environment. That is to say, the microphone may be positioned within wearable word counter 100 such that the microphone will detect any spoken words that would be heard by the user, for example. Audio input waveform 205 shows a representation of three syllables spoken by, for example, a parent to a small child as detected by a microphone within analog input receiver 115 shown in FIG. 1.

After analog input receiver 115 receives analog input, one or more linear analog filters 120 remove undesirable portions of the analog input signal. Although referred to in the plural, linear analog filters 120 may be implemented as a single filter or in combinations of various filters. Linear analog filters 120 may be implemented as low pass filters, high pass filters, all pass filters, band pass filters, band reject filters, and any other type of analog filter. Linear analog filters 120 may, for example, be implemented to remove portions of the analog input that fall outside the hearing ability of a human being. For example, linear analog filters may filter out any portions of analog input above 20 kHz, leaving the portion of the analog input between 0 Hz and 20 kHz. Linear analog filters 120 may be implemented in such a way as to remove noise from the analog input. Linear analog filters 120 may be further implemented in such a way as to remove portions of the analog input that would be inconsistent with human speech. For example, the frequency range of voiced speech typically occurs in the range of 100 Hz to 3 kHz. Linear analog filters 120 may be implemented to remove any portion of the analog input that falls outside the range of 100 Hz to 3 kHz, for example. Any particular implementation of linear analog filters 120 may be implemented to meet any desirable range of analog input received by analog input receiver 115. Filtered audio input waveform 210 of FIG. 2 shows the same three syllables that are shown in audio input waveform 205 after those words have been subjected to filtering via linear analog filters 120.

Once filtering is complete, a filtered signal is produced by linear analog filters 120 and is provided to gain amplifier stage 125. Gain amplifier stage 125 is used to amplify and enhance the filtered signal. Amplifying the filtered signal increases the amplitude of the filtered signal and makes the filtered signal large enough to measure or compare to a threshold, as will be discussed below. For example, amplified filtered waveform 215 shown in FIG. 2 shows clearly three distinct syllables that were received as analog input, filtered by the linear analog filters 120, and amplified in gain amplifier stage 125. This amplified signal is provided to envelope detector 130.

Envelope detector 130 operates as a waveform smoothing function on the amplified signal provided to envelope detector 130. Generally, a capacitor is slowly charged and discharged by the amplified signal, which produces a waveform similar to that shown as envelope waveform 220, shown in FIG. 2. Thus, envelope detector 130 removes each frequency spike of the original analog input in favor of providing a smoothed waveform representative of the three syllables originally spoken to the user of wearable word counter 100. Envelope detector 130 provides this smoothed signal to threshold detector 135. The term "smooth waveform" or "smoothed waveform" means a waveform substantially free from frequency spikes. One example of a smoothed waveform is shown as envelope waveform 220, shown in FIG. 2.

Threshold detector 135 applies a threshold level to the smoothed signal to determine what portions of the analog input do and do not correspond to a spoken syllable. In one embodiment, threshold detector 135 may be implemented as a voltage detector or a current detector implemented as voltage comparators. Other types of threshold detectors are possible. In practice, threshold detector 135 detects any portion of the smoothed signal generated by envelope detector 130 that exceeds a particular amplitude (current or voltage). As shown in FIG. 2, threshold waveform 225 denotes that the smoothed signal shown in envelope waveform 220 exceeds the threshold amplitude in three portions of threshold waveform 225. Threshold detector 135 converts the smoothed signal into a square wave, showing the three syllables spoken to the user and eliminating any portion of the smoothed signal that does not meet or exceed the particular amplitude determined to correspond to a syllable of speech. The square wave is provided by threshold detector 135 to syllable detector 140.

Syllable detector 140 is implemented by a processor in digital microcontroller circuit 110. The processor in digital microcontroller circuit 110 within wearable word counter 100 can include a combination of one or more application programs and one or more hardware components. For example, application programs may include software modules, sequences of instructions, routines, data structures, display interfaces, and other types of structures that execute operation. Further, hardware components may include a combination of processors, microcontrollers, busses, volatile and non-volatile memory devices, non-transitory computer readable memory device and media, data processors, control devices, transmitters, receivers, antennas, transceivers, input devices, output devices, network interface devices, and other types of components that are apparent to those skilled in the art.

Syllable detector 140 receives the square wave from threshold detector 135 and compares the square wave received from threshold detector 135 against a square wave duration threshold. Any square wave with a duration less than a minimum time duration threshold is discarded. Similarly, any square wave with a duration greater than a maximum time duration threshold is also discarded. Any square wave with a duration greater than the minimum time duration threshold and less than the maximum time duration threshold is representative of a syllable spoken to a user of wearable word counter 100. Accordingly, syllable detector 140 aggregates the number of syllables spoken to the user. Typically, adults speak to babies using monosyllabic words. Thus, the syllable to counted word ratio spoken to a baby may be approximately 1:1. However, as a child grows, adult speech directed to the child gains complexity, using both monosyllabic and polysyllabic words. Thus, as a baby grows into a child, the number of syllables per individual word spoken to the child increases. Accordingly, syllable detector 140 may monitor the age of the user and adjust the syllable to counted word ratio to count the number of words spoken to the user of wearable word counter 100 as a child grows from infancy.

For example, adults speaking to babies may not use complete sentences. An adult speaking to a baby may point to a dog and say "dog, dog, dog" while an adult speaking to a toddler may point to a dog and say "do you see the furry puppy?" In such a case, the adult's speech directed to a toddler is substantially more complex than the adult's speech directed to the baby. Accordingly, wearable word counter 100 may adjust the counting of words to account for more complex speech by adjusting the syllable to counted word ratio. For a baby younger than 6 months old, in one hypothetical example, wearable word counter 100 may use a syllable to counted word ratio of one syllable to one counted word (i.e., one syllable is counted as one word). For a baby older than 6 months, in another hypothetical example, wearable word counter 100 may use a syllable to counted word ratio of 1.5 syllables to one counted word (i.e., for every 1.5 counted syllables, one word is counted). For babies older than a year, in another hypothetical example, wearable word counter 100 may use a syllable to counted word ratio of 2 syllables to one counted word (i.e., for every 2 counted syllables, one word is counted). Syllable detector 140 may adjust this syllable to counted word ratio based on the age of the user of wearable word counter 100.

Syllable detector 140 constantly monitors speech directed to the user of wearable word counter 100 and counts the syllables detected. Once syllable detector 140 applies the syllable to counted word ratio, a number of words spoken to the user is determined. In one embodiment, this number of words spoken to the user may be transmitted by wearable word counter 100 to a mobile device. Any mobile device may be suitable for receiving information from wearable word counter 100. Conventional mobile devices include devices that are capable of running a software application, such as a smart phone, a tablet, a personal computer, a desktop computer, a music storage and playback device, a personal digital assistant, or any other device capable of implementing a software application.

In one embodiment, digital microcontroller circuit 110 (and/or syllable detector 140) may automatically adjust an amplification and a threshold level for received audio input based on ambient noise in a particular aural environment. For example, in a noisy room, digital microcontroller circuit 110 may sample the aural environment to determine a "noise floor" for that environment. The noise floor may also be referred to as ambient noise. During speech, the ambient noise is increased. In order to recognize speech in relatively noisy aural environments, digital microcontroller circuit 110 may adjust the amplification and threshold levels discussed above such that only speech directed to the user of wearable word counter 100 meets or exceeds the adjusted threshold level. This automatic adjustment ensures that the syllable count remains accurate because ambient noise falls short of meeting an automatically set threshold for a particular aural environment. Thus, ambient noise is not reflected in the syllable count.

In another embodiment, wearable word counter 100 may transmit information to one or both of a mobile device and a non-mobile device. For example, wearable word counter 100 may be provided with a docking station designed to remain tethered to a non-mobile power supply. The docking station may operate using alternating current power supplied from an electrical outlet in, for example, a home. In one embodiment, the docking station may be configured to recharge the battery or batteries within wearable word counter 100 when the docking station is connected to wearable word counter 100. The docking station may receive information from wearable word counter 100 wirelessly, through a wired connection, and/or through a corresponding male and female connector disposed within wearable word counter 100 and the docking station. The docking station may have a separate ability to connect to a mobile device, a server, a cloud computer, or any other device using a wired or wireless connection to provide information received from wearable word counter 100 to other devices. The mobile device may display information, including word count information, received from wearable word counter 100. The docking station may further implement any functionality of the mobile device described herein.

In one embodiment, wearable word counter 100 may connect to the mobile device or to the non-mobile device using a wireless communication connection. For example, a wireless communication connection may be implemented using a Bluetooth wireless communication link. Numerous other types of communication links may also be implemented including Wi-Fi, ZigBee, Z-Wave, RF4CE, Ethernet, telephone line, cellular channels, or others that operate in accordance with protocols defined in IEEE (Institute of Electrical and Electronics Engineers) 802.11, 801.11a, 801.11b, 801.11e, 802.11g, 802.11h, 802.11i, 802.11n, 802.16, 802.16d, 802.16e, or 802.16m using any network type including a wide-area network ("WAN"), a local-area network ("LAN"), a 2G network, a 3G network, a 4G network, a Worldwide Interoperability for Microwave Access (WiMAX) network, a Long Term Evolution (LTE) network, Code-Division Multiple Access (CDMA) network, Wideband CDMA (WCDMA) network, any type of satellite or cellular network, or any other appropriate protocol to facilitate communication between wearable word counter 100 and the mobile device.

In one embodiment, the mobile device may be used to interface with wearable word counter 100. For example, in addition to receiving a real-time transmission of the number of words spoken to a user of wearable word counter 100, the mobile device may additionally allow another user, such as a parent of a child wearing wearable word counter 100, to make adjustments in the settings of wearable word counter 100. For example, the parent may manually adjust the syllable to counted word ratio to more accurately reflect the level of speech complexity heard by the child for a particular duration of time. For example, a parent may use a mobile device to adjust the syllable to counted word ratio down if a toddler were to experience a play date with other toddlers for the duration of the playdate (because other toddlers will use less complex speech to interact with other toddlers). In another embodiment, the mobile device recommends a particular syllable to counted word ratio to be implemented by wearable word counter 100 during a particular time.

One benefit of connecting wearable word counter 100 to a mobile device is accessing the enhanced processing power of the mobile device. Mobile devices typically have much more advanced processing capabilities than wearable word counter 100, which allows for more complex analysis of speech and speech patterns. Accordingly, wearable word counter 100 may, in addition to counting the number of words spoken to a child, stream the analog input to the mobile device for more complex analysis in a compressed or uncompressed format. In one embodiment, wearable word counter 100 may apply initial filtering and amplification to the analog input with linear analog filters 120 and gain amplifier stage 125 before streaming a filtered and amplified representation of the analog input to the mobile device. In another embodiment, wearable word counter 100 may intermittently stream the analog input at different times during use in order to provide the mobile device of an averaged sample of the analog input. In one embodiment, wearable word counter 100 records analog input and transmits the analog input as an analog signal to the mobile device via the wireless communication connection.

In another embodiment, the mobile device records an analog signal representative of voiced speech directed to a user of wearable word counter 100 provided over the wireless communication connection by wearable word counter 100. The mobile device may transmit the recorded analog signal to a server or to a cloud computer for more advanced speech processing or perform speech analysis in the mobile device. In another embodiment, wearable word counter 100 may stream an analog signal representative of voiced speech directed to a user of wearable word counter 100 over a wireless communication connection directly to a cloud computer, without transmitting the analog signal through the mobile device. In these ways, more complex analysis of the speech heard by or spoken to the user may be performed. This more complex analysis may provide a mobile phone user (or a cloud computer user) with information such as the number of times a user of wearable word counter 100 has heard a particular word or identify commonly used conversational terms, identify the language or languages spoken to the user of wearable word counter 100, and other similar analysis. The mobile device may also update the firmware within wearable word counter 100 via the wireless communication connection between the mobile device and wearable word counter 100.

Finally, wearable word counter 100 may further include a light sensor and an accelerometer. In one embodiment, wearable word counter 100 may determine, via a light sensor, that the user is watching television based on the flickering light emitted by the television. Wearable word counter 100 may exclude words that are detected during periods when the light sensor detects the flickering light emitted by a television. In one embodiment, a light sensor may further be used to detect an ambient light level in the environment around wearable word counter 100. Wearable word counter 100 may determine that a certain level of light, or lack thereof, indicates that the user of wearable word counter 100 may be asleep or going to sleep. Accordingly, wearable word counter 100 may determine, based on the detected ambient level of light, that no words are likely to be spoken to the user and enter an off state or a power stand-by state or discontinue streaming audio information in order to save battery power. In another embodiment, wearable word counter 100 may infer a state of a user based on the user's movement, as detected by the accelerometer. If the user is moving, for example, wearable word counter 100 may stream audio to the mobile device. However, if the user is not moving, as detected by the accelerometer, wearable word counter 100 may infer that the user is asleep and stop the streaming audio information until the user awakes. Wearable word counter may also enter an off state or a power stand-by state in order to save battery power during periods when the user's movements are less frequent or reduced.

Figure 3:
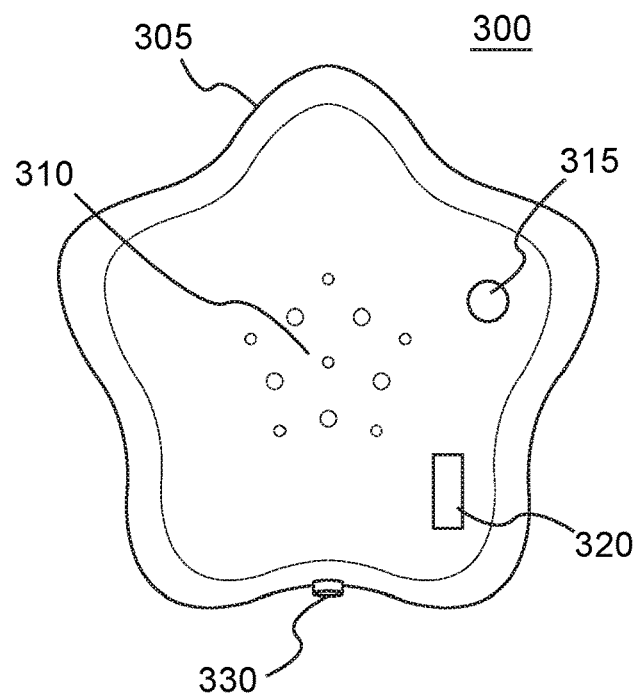
FIG. 3 illustrates an exemplary wearable word counter.

FIG. 3 illustrates an exemplary embodiment of wearable word counter 300. Wearable word counter 300 may include a housing 305 which may, or may not, be formed in a fanciful shape. Housing 305 is shown as being formed in the shape of a star, in the example of FIG. 3, although other shapes are possible. Housing 305 may include a number of perforations to accommodate a microphone 310 disposed within housing 305. As previously discussed, wearable word counter 300 may further include a light sensor 315 disposed within housing 305 that provides information and input about the amount of light in the environment around wearable word counter 300 to a processor disposed within wearable word counter 300, such as a processor disposed within digital microcontroller circuit 110 discussed above with respect to FIG. 1. Wearable word counter 300 may further include an accelerometer 320 disposed within housing 305 that provides information and input about the amount or total amount of movement in three dimensional axes (X, Y, and Z in the Cartesian sense) associated with a wearer of wearable word counter 300 to a processor disposed within wearable word counter 300, such as a processor disposed within digital microcontroller circuit 110. It is assumed that, when worn, movement of wearable word counter 300 is commensurate with movement of a wearer of wearable word counter 300. Wearable word counter 300 may further include a button 330 that allows a user to interface with wearable word counter 330 directly, or via a mobile device.

In one embodiment, wearable word counter 300 may employ microphone 310 to record one or more words spoken in an environment of a wearer of wearable word counter 300. Further, wearable word counter 300 may employ microphone 310 in combination with light sensor 315 and accelerometer 320 to determine the quality and intentionality of the one or more spoken words. For example, in one embodiment, wearable word counter 300 itself, or in combination with a mobile device, may identify whether or not a wearer of wearable word counter 300 is moving via accelerometer 320 and how much light is in the wearer of the wearable word counter's environment.

In this manner, a wearable word counter 300 may identify that wearer of the wearable word counter 300 is likely to be awake because there is a bright light in the wearer of the wearable word counter's environment, and substantial movement is being detected via accelerometer 320. Given that a wearer of wearable word counter 300 is likely to be awake because of the level of light and the level of movement associated with the wearer, wearable word counter 300 wearable word counter 300 may determine, using the techniques described herein, that a speaker is speaking to the wearer of wearable word counter 300. Alternatively, wearable word counter 300 may detect speech, low light, and little movement via microphone 310, light sensor 315, and accelerometer 320, respectively and determine that the wearer of wearable word counter 300 is likely asleep. Based on the determination that the wearer of wearable word counter 300 is likely asleep, wearable word counter may determine that it should not count the number of words spoken to the wearer of wearable word counter 300. In other words, speech that is spoken to the wearer of wearable word counter 300 when the wearer of wearable word counter 300 is asleep may be identified as low quality speech or speech that is not intentionally spoken to a child and may, therefore, not be counted as words heard by the wearer of wearable word counter 300.

Wearable word counter 300 may further detect repeatable trends in a wearer of wearable word counter's daily schedule in order to identify speech that is intended to be spoken to the child at a particular time of day. In other words, if wearable word counter 300 detects that the amount of light in the environment of a wearer of wearable word counter 300 decreases every afternoon at 2:00 and further detects that the amount of movement associated with the wearer of wearable word counter 300 substantially decreases every afternoon at 2:00, wearable word counter 300 may determine that 2:00 is a likely nap time for the wearer of the wearable word counter. In response, wearable word counter 300 may determine that speech detected during periods associated with these repeatable trends should not be counted as speech spoken to a wearer of wearable word counter 300. Alternatively, wearable word counter 300 may detect that the amount of light in the environment of the wearer of wearable word counter 300 increases every morning around 9:30 and further detects that the amount of movement associated with a wearer of wearable word counter 300 substantially increases every morning at 9:30. In response, wearable word counter 300 may determine that the wearer of wearable word counter 300 wakes up each morning at approximately 9:30 and begin identifying and counting words spoken to the wearer of wearable word counter 300.

In another embodiment, wearable word counter 300 may detect and identify multiple speakers (e.g., two or more speakers) in a conversation via microphone 310. For example, wearable word counter 300 may, in combination or independently of a mobile device, identify the frequency or pitch rate of various speakers in a spoken conversation. Since adult women typically speak in a higher vocal register, adult women typically vocalize at relatively higher frequencies. Similarly, adult men typically speak in a lower vocal register and typically vocalize at relatively lower frequencies than women. The term "identify" as used with respect to "identify[ing] multiple speakers" is to be construed as identifying or determining the number of people in a conversation.

In one embodiment, a processor within digital microcontroller circuit 110 of wearable word counter 300 may analyze speech detected via microphone 310 to identify whether an adult woman or an adult man are involved in a conversation. Further, the processor within digital microcontroller circuit 110 of wearable word counter 300 may identify various speakers by consistent detection of similar frequencies over time. For example, a mother of a child who is wearing wearable word counter 300 may frequently be detected as a speaker. Wearable word counter 300 may identify, through a frequency analysis of detected speech performed by the processor within digital micro controller circuit 110, that, for example, an adult woman speaking in a particular or specific frequency range as a child's mother, essentially identifying the adult woman by consistently identifying the frequency (pitch) of the mother's speech. Wearable word counter 300 may similarly identify fathers, caregivers, grandparents, siblings, friends, and other children in a similar fashion.

In this example, wearable word counter 300 may identify individual people in the life of a wearer of wearable word counter 300 and recognize a higher quality level of spoken words by these individuals interacting with the wearer of wearable word counter 300. It should be noted that adults can manipulate the pitch of their voice, especially when first seeing a small child, and that may cause wearable word counter 300 to misidentify a particular individual. Thus, wearable word counter 300 may continually identify commonalities in frequency and pitch of a particular speaker's speech over time to correctly identify one or more speakers in a conversation.

Figure 4:
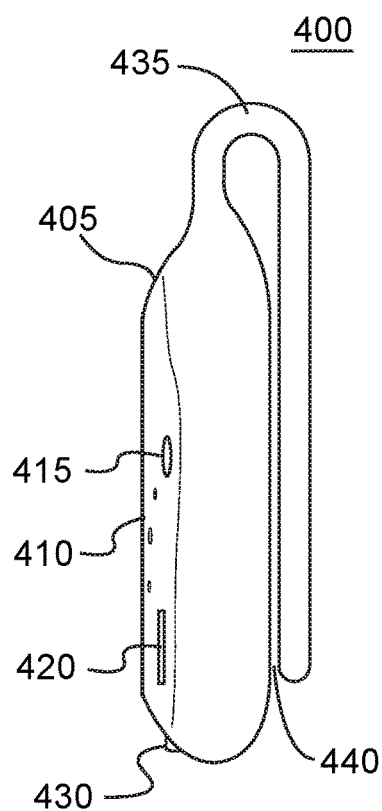
FIG. 4 illustrates an exemplary wearable word counter with a clothing clip accessory.

FIG. 4 illustrates an exemplary wearable word counter 400 with a clothing clip accessory 435. Wearable word counter 400 may be similar to wearable word counter 100, shown in FIG. 1 and wearable word counter 300, shown in FIG. 3. Wearable word counter 400 may be include a housing 405 within which are disposed a microphone 410, a light sensor 415, and an accelerometer 420. Wearable word counter 400 may further include an interface button 430 that allows a user to interface with wearable word counter 430 directly, or via a mobile device.

Wearable word counter 400 may be installed within clothing clip accessory 435. Clothing clip accessory 435 may be fashioned using a pliable plastic, such as silicone plastic, to provide a form fit for housing 405. Clothing clip accessory 435 may further include a rigid clothing clip which is designed to attach to clothing associated with a wearer of wearable device 400. Clothing clip accessory 435 may include a gap 440 that allows clothing clip accessory 435 to be attached to a wearer's clothing in a pocket, on a belt, in the pants, in a neck hole, on a shoe, or another similar element of clothing. For example, clothing clip accessory 435 may be slid over a neck hole in a child's onesie by inserting a seam around the neck hole of the onesie through gap 440 such that clothing clip accessory 435 is disposed on an inside of the child's onesie while holding wearable word counter 400 on the outside of the child's onesie.

By attaching wearable word counter 400 to a child's clothing, wearable word counter 400 is in place to accurately detect speech, via microphone 410, light levels in the child's environment, via light sensor 415, and a level of activity for the child, via accelerometer 420. Advantageously, wearable word counter 400 may also be in place to detect vocalizations made by a child. In one embodiment, wearable word counter 400 may detect and identify crying noises associated with the child wearing wearable word counter 400.

Crying noises made by young children are typically very high in pitch, relative to other vocalizations made by young children, very persistent, and very loud. Thus, crying noises may be detected by wearable word counter 400 identifying vocalizations that include vocalizations with a duration greater than a single syllable threshold, higher than usual pitch, and the lack of another speaker identified as being in the environment, as discussed above with respect to FIG. 3. In one embodiment, wearable word counter 400 may identify an amount of time for which a child has been crying over a particular time period, such as a duration of a babysitter's visit, a day, a week, a month, or etc. Wearable word counter 400 may be configured to provide messages to a parent or caregiver to notify them that a child has been crying for a certain amount of time. For example, wearable word counter 400 may be configured to transmit a message to a parent that a child has been crying for 20 minutes, especially when the parent is away from the child to allow a parent to follow up with a babysitter or other caregiver.

In another embodiment, wearable word counter 400 may detect crying and identify a relative amount of light associated with a child's location and may identify a relative amount of movement associated with the child. In this manner, for example, wearable word counter 400 may identify an amount of time taken by a child to fall asleep once in bed. Wearable word counter 400 may compare the identified amount of time taken by a child to fall asleep once in bed to show a child's improvement over time.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A word counter device, comprising:
   a microphone which receives speech input;
   a light sensor; and
   an accelerometer, wherein the microphone, the light sensor, and the accelerometer are disposed within a housing of the word counter device
   a processor, disposed within the housing of the word counter device, which generates data representative of one or more syllables detected by the microphone from the speech input received through the microphone,
   wherein based on one or more of speech input received via the microphone disposed within the word counter device, input from the light sensor indicating an amount of light in an environment around the word counter device, and movement input from the accelerometer disposed within the housing of the word counter device, the processor identifies whether a particular spoken word is directed towards a wearer of the word counter device, and
   wherein the speech input received via the microphone disposed within the word counter device includes data representative of one or more frequencies of one or more syllables detected by the microphone.

2. The word counter device of claim 1, wherein, based on the data representative of one or more syllables generated by the processor, the processor identifies a number of words in the received speech input.

3. The word counter device of claim 2, wherein the processor identifies speech input received via the microphone as crying.

4. The word counter device of claim 3, wherein the processor identifies speech input received via the microphone as crying by detecting the presence of only a single speaker in the aural environment.

5. The word counter device of claim 1, wherein the processor receives input from the light sensor indicating an amount of light in an environment around the word counter device.

6. The word counter device of claim 1, wherein the processor receives movement input from the accelerometer disposed within the housing of the word counter device.

7. The word counter device of claim 1, wherein input from the accelerometer disposed within the housing of the word counter device includes data representative of the wearer of the word counter device's movements in three dimensional axes.

8. The word counter device of claim 1, wherein, based on one or more of speech input received via the microphone disposed within the word counter device, input from the light sensor indicating an amount of light in an environment around the word counter device, and movement input from the accelerometer disposed within the housing of the word counter device, the processor identifies whether or not a wearer of the word counter device is asleep.

9. The word counter device of claim 1, wherein the processor identifies one or more speakers in a conversation based on the data representative of one or more frequencies of one or more syllables detected by the microphone.

10. The word counter device of claim 1, wherein the processor identifies a particular speaker by associating an identified frequency range within the data representative of one or more frequencies of one or more syllables detected by the microphone with a particular speaker.

11. The word counter device of claim 1, wherein the processor identifies speech input received via the microphone as crying by detecting a duration of one or more vocalization pulses as exceeding a syllable duration threshold.

12. A word counter system, comprising:
   a word counter device, comprising:
      a microphone which receives speech input;
      a light sensor;
      an accelerometer; and
      a processor, where each of the microphone, the light sensor, the accelerometer, and the processor are disposed within the housing of the word counter device,
      wherein based the speech input received via the microphone disposed within the word counter device, input from the light sensor indicating an amount of light in an environment around the word counter device, and movement input from the accelerometer disposed within the housing of the word counter device, the processor identifies whether a particular spoken word is directed towards a wearer of the word counter device, and
      wherein the speech input received via the microphone disposed within the word counter device includes data representative of one or more frequencies of one or more syllables detected by the microphone, and
   a mobile device, wherein the processor generates data representative of one or more syllables detected by the microphone from the speech input received through the microphone and provides the data representative of the one or more syllables to the mobile device.

13. The word counter system of claim 12, wherein the mobile device receives input from the light sensor indicating an amount of light in an environment around the word counter device.

14. The word counter system of claim 12, wherein the mobile device receives movement input from the accelerometer disposed within the housing of the word counter device.

* * * * *